(12) United States Patent
Huang (10) Patent No.: US 10,056,423 B1
(45) Date of Patent: Aug. 21, 2018

(54) MULTISPECTRAL IMAGING DEVICE

(71) Applicant: EXPANTRUM OPTOELECTRONICS, Shanghai (CN)

(72) Inventor: Zhongshou Huang, Shanghai (CN)

( * ) Notice: Subject to any disclaimer, the term of this patent is extended or adjusted under 35 U.S.C. 154(b) by 0 days.

(21) Appl. No.: 15/809,040

(22) Filed: Nov. 10, 2017

(30) Foreign Application Priority Data

Jul. 11, 2017 (CN) .......................... 2017 1 0559669

(51) Int. Cl.
| | | |
|---|---|---|
| *H01L 27/146* | (2006.01) | |
| *H01L 31/103* | (2006.01) | |
| *H01L 31/105* | (2006.01) | |
| *H04N 5/30* | (2006.01) | |
| *H04N 5/33* | (2006.01) | |
| *A61B 5/00* | (2006.01) | |

(52) U.S. Cl.
CPC ...... *H01L 27/14652* (2013.01); *A61B 5/0075* (2013.01); *H01L 27/1461* (2013.01); *H01L 27/1462* (2013.01); *H01L 27/14609* (2013.01); *H01L 27/14612* (2013.01); *H01L 27/14621* (2013.01); *H01L 27/14623* (2013.01); *H01L 27/14636* (2013.01); *H01L 27/14647* (2013.01); *H01L 31/103* (2013.01); *H01L 31/105* (2013.01); *H04N 5/30* (2013.01); *H04N 5/33* (2013.01); *H04N 5/332* (2013.01)

(58) Field of Classification Search
CPC ......... H01L 27/14649; H01L 27/14647; H01L 27/14652; H01L 27/14669; H01L 27/14601; H01L 27/14636; H01L 31/103; H01L 31/105; H01L 27/1462; H01L 27/14621; H01L 27/14623; H01L 27/14609; H01L 27/1461; H01L 27/14612; H04N 5/30; H04N 5/33; H04N 5/332
See application file for complete search history.

(56) References Cited

U.S. PATENT DOCUMENTS

2017/0310917 A1* 10/2017 Kurokawa ........ H01L 27/14649

* cited by examiner

*Primary Examiner* — Thanhha Pham (57) ABSTRACT

A multispectral imaging device, comprising a pixel array, each said pixel comprises at least a first subpixel and a second subpixel, each subpixel comprises at least an infrared light conversion layer; a visible light conversion layer and a color filter layer; said visible light conversion layer is arranged between said infrared light conversion layer and said color filter layer; wherein, infrared conversion efficiency in said first subpixel is larger than infrared conversion efficiency in said second subpixel, and infrared light transmittance of the color filter layer in said first subpixel is larger than infrared light transmittance of the color filter layer in said second subpixel. The multispectral imaging device realizes imaging in multiple wavebands and in an increased dynamic range.

21 Claims, 9 Drawing Sheets

| wavelength um | energy eV | wavelength um | energy eV |
|---|---|---|---|
| 0.4 | 3.1 | 0.78 | 1.59 |
| 0.42 | 2.95 | 0.8 | 1.55 |
| 0.44 | 2.82 | 0.82 | 1.51 |
| 0.46 | 2.7 | 0.84 | 1.48 |
| 0.48 | 2.58 | 0.86 | 1.44 |
| 0.5 | 2.48 | 0.88 | 1.41 |
| 0.52 | 2.38 | 0.9 | 1.38 |
| 0.54 | 2.3 | 0.92 | 1.35 |
| 0.56 | 2.21 | 0.94 | 1.32 |
| 0.58 | 2.14 | 0.96 | 1.29 |
| 0.6 | 2.07 | 0.98 | 1.27 |
| 0.62 | 2 | 1 | 1.24 |
| 0.64 | 1.94 | | |
| 0.66 | 1.88 | | |
| 0.68 | 1.82 | | |
| 0.7 | 1.77 | | |
| 0.72 | 1.72 | | |
| 0.74 | 1.68 | | |
| 0.76 | 1.63 | | |

MULTISPECTRAL IMAGING DEVICE

CROSS REFERENCE

This application is based upon and claims the benefit of priority from Chinese Patent Application No. 201710559669.8 filed on Jul. 11, 2017, the entire contents thereof are incorporated herein by reference.

TECHNICAL FIELD

The present disclosure belongs to the field of medical diagnosis instrument, specifically to a multispectral imaging device.

BACKGROUND

Subcutaneous structures and blood vessels under skin are barely visible for naked eyes directly. Without any medical instrument, medical doctors can only rely on the external outline of human body and their anatomic knowledge to recognize and locate subcutaneous structures and blood vessels.

The blood vessels, comprising veins and arteries, are hidden below the epidermis and dermis, and in some cases mixed with the subcutaneous fat or are even behind the bones. Images of the blood vessels under the visible light illumination are therefore extremely faint and barely visible for naked eyes. Before puncture, the doctors often try to make the blood vessels more visible by asking the patients to clench their fist or flapping the skin above the blood vessel, but hindered by patients' age and the thickness of subcutaneous fat and etc., the visibility of subcutaneous blood vessels is still not satisfying in most case. Injections relying on the barely visible images of blood vessels frequently results misalignment of the puncture, causing unnecessary pain in patients and delaying optimal time for medical treatment, even triggering other serious side effect. Apart from blood drawing and injection acted on blood vessels directly, acupuncture and other medical surgery etc. all need the blood vessels to be located accurately, so the blood vessels can be avoided or be treated respectively.

In recent years, a technical approach based on near-infrared (NIR) imaging technology for solving the problem has been proposed. This technical approach is based on the fact that the absorption coefficient of hemoglobin for NIR light from 760 nm and 1000 nm is different from that of other human tissues around the veins, so image contrast is built up. To implement this technical approach, NIR images of veins are acquired in the first step, then the infrared image is digitized and enhanced in contrast and signal to noise ratio by an image processing unit, enhanced image is finally projected back to human skin surface by a visible light projection device. In this technical approach, which has augment reality effect in a broad meaning, the doctors and nurses are able to recognize and locate precisely the subcutaneous blood vessels and conduct various medical treatments and operate in real time.

However, the subcutaneous blood vessels are surrounded by subcutaneous fat and muscular tissues, inevitably causing strong scattering to the infrared image. To add more obstacles, wrinkles, scars and hairs on the skin surface all have strong absorption and scattering effects to attenuate and blur the infrared image. These drawbacks become severe when imaging objects are narrow branches of blood vessels and capillaries. This is simply because that less blood volume and therefore less hemoglobin are in the infrared light path, while the light scatterings from surrounding tissues remain the same, resulting less absorption and faint contrast in infrared image. Under the influence of scattering light, the image contrast of the blood vessels to the surrounding tissues is often observed in the range of 0.01~0.1. An ordinary method to boost up image contrast is to simply irradiate stronger light onto the image objects. But this method will bring back stronger background scattering of infrared light, which may cause the image device deviated from linear response range or even fully saturated by the flood of light. Adoption of imaging device with higher gain may improve the signal-to-noise ratio to some extent, but will cause the image device saturated earlier or in other words less dynamic range.

SUMMARY

The primary purpose of the present disclosure is to provide a multispectral imaging device to realize multispectral imaging with a wide dynamic range.

According to one aspect of the present disclosure, a multispectral imaging device is provided, the pixel array comprises a plurality of pixels arranged repeatedly and periodically, each pixel at least comprises a first subpixel and a second subpixel, each of the subpixels at least comprises: an infrared light conversion layer to convert NIR light photons to electrons; a visible light conversion layer to convert visible light photons to electrons; a color filter layer to selectively transmit light of specific color; the visible light conversion layer is arranged between the infrared light conversion layer and the color filter layer. The conversion efficiency of the infrared light conversion layer of the first subpixel is larger than the conversion efficiency of the infrared light conversion layer of the second subpixel, in addition the infrared light transmittance of the color filter layer of the first subpixel is larger than the infrared light transmittance of the color filter layer of the second subpixel.

According to another aspect of the present disclosure, a multispectral imaging device as described above is provided, wherein at least one of the subpixel further comprises: an interlayer transparent conductive film, arranged between the visible light conversion layer and the infrared light conversion layer to shield electric field between the visible light conversion layer and the infrared light conversion layer, and to increase the charge capacity of both the visible light conversion layer and the infrared light conversion layer; the interlayer transparent conductive film is connected to an inner or external controllable potential; the transmittance of the interlayer transparent conductive film in the NIR light is greater than 50%.

On that account, by providing the arrangement in color filters with different transmission and infrared subpixels with different sensitivity, the multispectral imaging device of the present disclosure is capable of handing broader range of signal dynamic range and spectral response. Another important application brought by the multispectral imaging device in this disclosure is that, multiple layers of infrared light image representing subcutaneous structure at different depths can be acquired in separate subpixels, and therefore scattering noise background can be removed, some critical image details can be extracted through image subtraction algorithms.

BRIEF DESCRIPTION OF THE FIGURES

By reading the detailed description of nonrestrictive embodiment referring to the figures below, the other features, objects and advantages will be more apparent.

DETAILED DESCRIPTION

In the following, embodiments of the present disclosure will be described in detail referring to figures. The concept and its realizations of the present disclosure may be implemented in a plurality of forms, and should not be understood to be limited to the embodiments described hereafter. On the contrary, these embodiments are provided to make the present disclosure more comprehensive and understandable, and so the conception of the embodiments may be conveyed to the person skilled in the art fully. Same reference numbers in the figures refer to same or similar structures, so repeated description of them will be omitted.

The features, structures or characteristics described may be combined in any appropriate way in one or more embodiments. In the description below, many specific details are provided to explain the embodiments of the present disclosure fully. However, the person skilled in the art should realize that, without one or more of the specific details, or adopting other methods, components, materials etc., the technical approach of the present disclosure may still be realized. In certain conditions, structures, materials or operations well known are not shown or described in detail so as not to obfuscate the present disclosure.

To overcome the drawbacks of existing technology, the present disclosure provides a multispectral imaging device comprising a pixel array, the pixel array comprises a plurality of pixels arranged repeatedly and periodically in space, each pixel comprises at least a first subpixel and a second subpixel, each subpixel comprises at least an infrared light conversion layer to convert NIR light photons to electrons; a visible light conversion layer to convert visible light photons to electrons; and a color filter layer to selectively transmit incident light of specific color, the visible light conversion layer is arranged between the infrared light conversion layer and the color filter layer; wherein, the conversion efficiency of the infrared light conversion layer of the first subpixel is larger than the conversion efficiency of the infrared light conversion layer of the second subpixel, and the infrared light transmittance of the color filter layer of the first subpixel is larger than the infrared light transmittance of the color filter layer of the second subpixel.

Below each embodiment of the present disclosure is described referring to a plurality of figures.

It should be stated that a plurality of embodiments described below along with their combinations and varieties, beyond doubt are within the scope of present disclosure.

Figure 1:
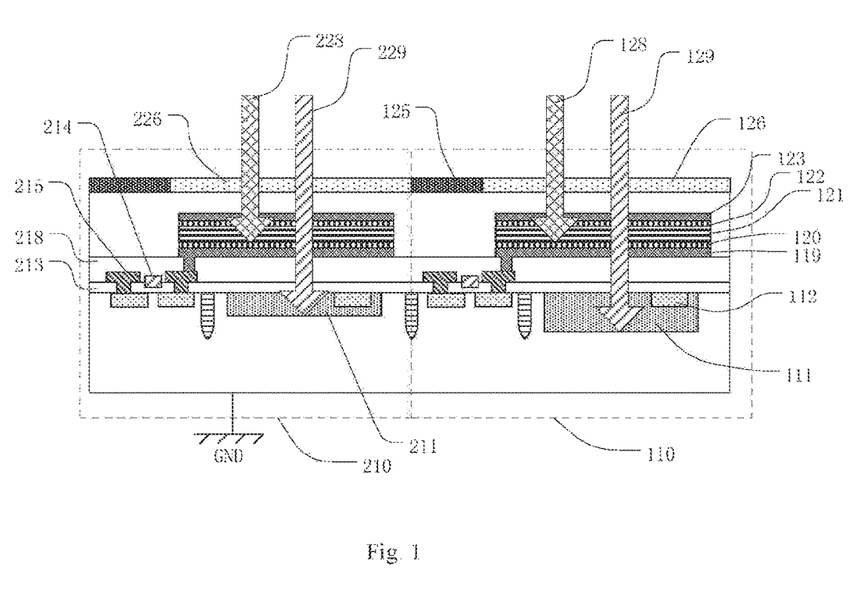
FIG. 1 is a cross-sectional view of a multispectral imaging device according to a first embodiment of the present disclosure.

FIG. 1 is a cross-sectional view of a multispectral imaging device of a first kind of embodiment of the present disclosure. The multispectral imaging device includes a plurality of pixels arranged repeatedly and periodically in space, each pixel includes at least a first subpixel 110 and a second subpixel 120. For the sake of simplicity, FIG. 1 only shows one first subpixel 110 and one second subpixel 120. Each subpixel (of the first subpixel 110 and the second subpixel 210) includes an infrared light conversion layer, a visible light conversion layer and a color filter layer. The visible light conversion layer is arranged between the infrared light conversion layer and the color filter layer.

The first photodiode (take the first photodiode of the first subpixel 110 as an example) comprises a semiconductor substrate and an electron depletion or hole depletion layer 111 formed in the semiconductor substrate. The electron depletion or hole depletion layer 111 may be composed of one or multiple doped layers which is fully or partially depleted in the semiconductor substrate. The first photodiode further comprises a heavily doped diffusion layer 112 for charge collection and transmission.

The second photodiode (take the second photodiode of the first subpixel 110 as an example) is in a form of multiple layers laminated in sequence, comprising a first transparent conductive film 119, a first doped layer 120, an un-doped a-Si layer 121, a second doped layer 122 and a second transparent conductive film 123.

The first transparent conductive film 119 is a lower transparent conductive electrode of the second photodiode, the material of the transparent electrode may be ITO, SnO2 etc. The first doped layer 120 and the second doped layer 122 may be the heavily doped layer of the second photodiode for ohmic contact with electrode 119 and 123, respectively. To form a p-i-n photodiode, if the first doped layer 120 is N+ conduction type, then the second doped layer 122 should be P+ conduction type and vice versa. During PECVD deposition process of the un-doped layer 121, doping material residues which is perhaps introduced during deposition of the first heavily doped layer 191, may be doped into layer 121. Consider the fact that the un-doped a-SiH film exhibits slightly weak N-type conductivity, it is preferred to have the first heavily doped layer 191 in P+ conduction type, so the layer 121 is compensated by very light P type dopant residue, and therefore end up with a true intrinsic semiconductor. One of the advantages of this deposition sequence is low dark current of a-SiH photodiode.

The second transparent conductive film 123 is deposited on top of the second photodiode, the material may be ITO, or SnO2, or other materials which are conductive and transparent for visible light and infrared light. In a preferable embodiment, the first photodiode is a PN type photodiode, the second photodiode is a PIN type photodiode. Other possible combinations and arrangements in the multispectral imaging device with the first photodiode and the second photodiode are beyond doubt within the scope of the present disclosure.

As shown in FIG. 1, each subpixel further comprises a switching transistor having gate electrode 214. The source electrode 215 of the switching transistor is connected to an output signal line, the drain electrode of the switching transistor is connected to the first transparent conductive film of the second photodiode. The source and drain electrodes of the switching transistor are made of metal, such as Cr, Mo, Al, Cu or an alloy thereof. The gate electrode 214 of the switching transistor may be made of polycrystalline silicon or metal, such as the metallic materials listed above or an alloy thereof. Switching transistor shown in FIG. 1 is one of the examples of various transistor structures, the person skilled in the art may also realize more varieties, it is no doubt that those varieties are within the scope of the present disclosure.

To separate different colors in visible light, and to separate visible light and NIR light, the multispectral imaging device are constructed in a manner that within the same subpixel, the color filter layer completely covers the visible light conversion layer, and the visible light conversion layer completely covers the infrared light conversion layer. With these arrangement color blending phenomenon is minimized. The color blending phenomenon could be caused by visible light in large incident angle, or by visible light reaching the infrared conversion layer.

Further, an opaque film 125 (or black matrix film that can be made of polyimide mixed with carbon powders) is arranged between adjacent filters, the width of the opaque film 125 is wider than or equal to the gap between adjacent visible light conversion islands in order to further block the light in large incident angle which could reach to neighborhood subpixel or could reach to infrared light conversion layer without being absorbed by visible light conversion layer.

In order to enlarge the discrepancy of infrared light sensitivity between the two subpixels, the conversion efficiency of the infrared light conversion layer of the first subpixel 110 is made larger than the conversion efficiency of the infrared light conversion layer of the second subpixel 210. In addition, the infrared light transmittance of the color filter layer of the first subpixel 110 is made larger than the infrared light transmittance of the color filter layer of the second subpixel 210.

To realize different infrared light sensitivities, infrared light conversion layers with different depths are employed in the subpixel and the second subpixel, respectively. More specifically, as shown in FIG. 1, infrared light conversion layer 111 in the first subpixel 110 is apparently deeper than the infrared light conversion layer 211 in the second subpixel 210.

Figure 2:
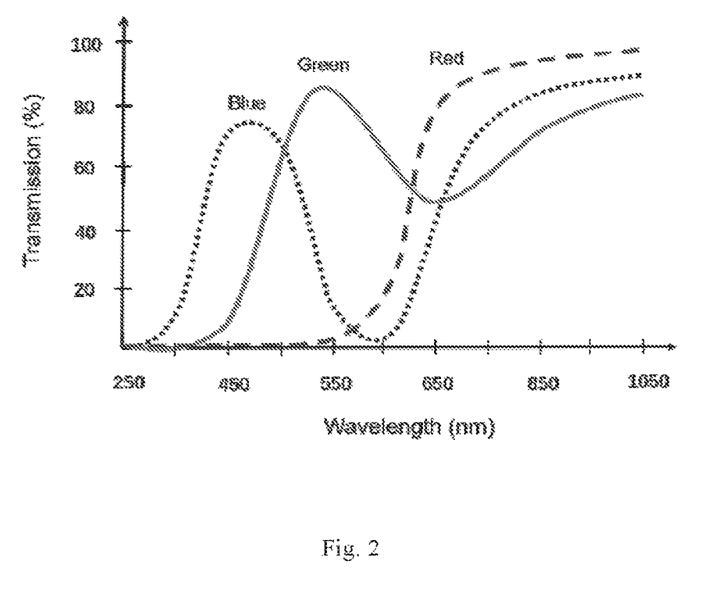
FIG. 2 is transmission spectral curves of RGB color filters of the present disclosure.

To realize different infrared light transmittance in color filter layers, as hinted in FIG. 2, selection of specific color filter maybe a readily applicable approach. Specifically, among the RGB three color filters, the red filter exhibits the highest transmittance in the NIR range, while the green filter exhibits the lowest transmittance in the NIR range. Hence, in the embodiment of FIG. 1, the red filter is chosen to be the filter 126 of the first subpixel 110; while the green or blue filter is the candidate to be the filter 226 of the second subpixel 120.

Figure 3:
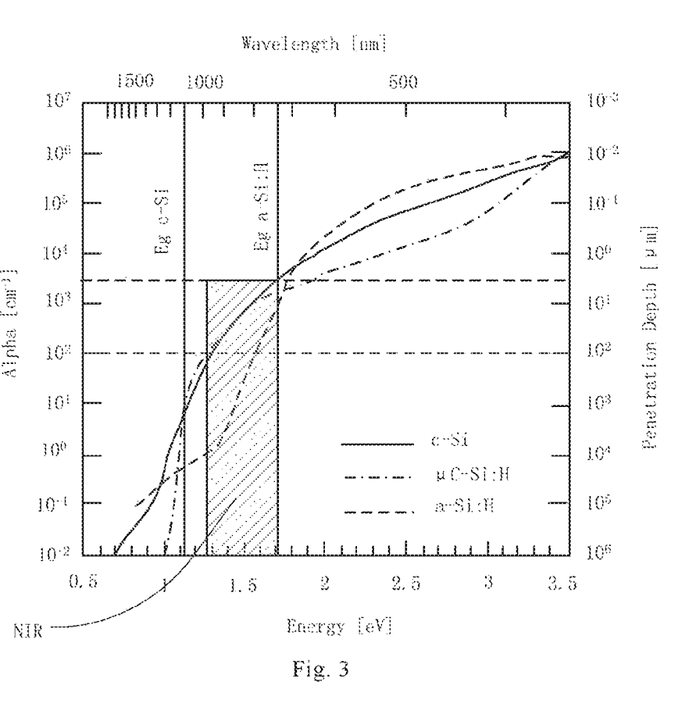
FIG. 3 is an illustration of absorption coefficient and penetration depths of visible light and infrared light in different silicon materials.
Figure 4:
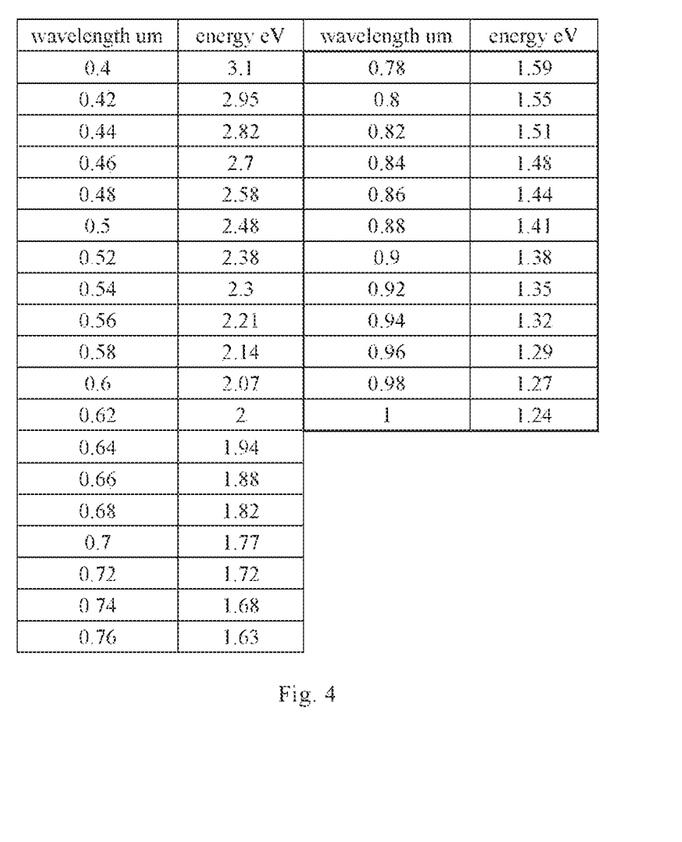
FIG. 4 is a table lists light wavelength and its corresponding photon energy.

FIG. 3 shows the absorption coefficient and penetration depth of radiation versus its wavelength in crystal silicon, micro-crystal silicon and in amorphous silicon, where the penetration depth is defined as the depth when light intensity drops to 1/2.7 of original level. As indicated in the figures, the band gap of a-SiH is about 1.6 eV~2.0 eV, the absorption in the photon energy from 1.24 eV to 1.7 eV is very small compared with crystal silicon, NIR light can easily pass through the a-SiH film and reach to the conversion layer in c-Si photodiode. Suggested by this diagram, To absorb most of the NIR light, particularly for the infrared light ranging 0.9 um to 1 um, the thickness of the depletion layer of c-Si photodiode should be 10 um to 100 um. In the embodiment shown in FIG. 1, the thickness of the depletion layer 111 of the first subpixel 110 may be 5 um to 50 um; the thickness of the depletion layer 211 of the first subpixel 120 may be 1 um to 20 um.

Combining the signal output from the first subpixel 110 featuring higher infrared light sensitivity and the signal output from the second subpixel 210 featuring higher saturation level, a large dynamic range infrared imaging sensor can be realized, which is further explained in the following by referring to FIG. 5.

Figure 5:
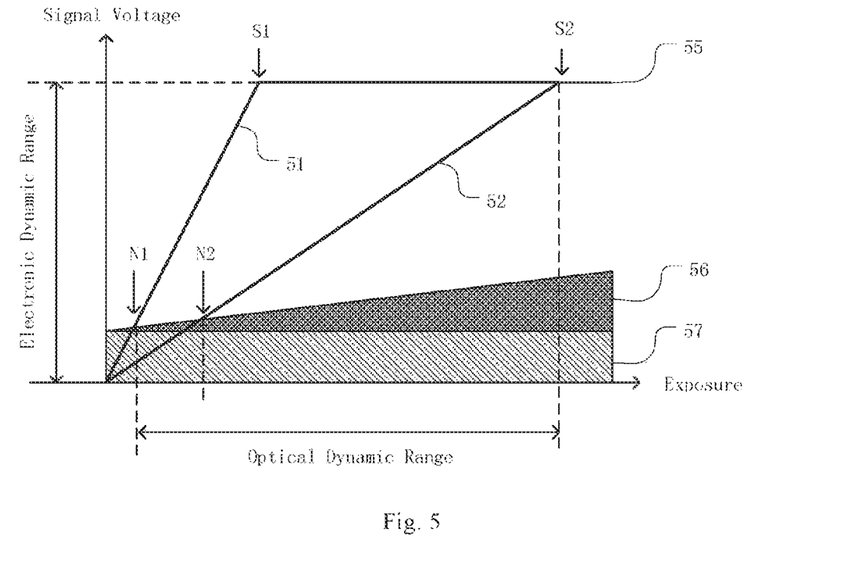
FIG. 5 is a illustration of the basic concept of wide dynamic range imaging with two infrared subpixels in the present disclosure.

As shown in FIG. 5, the reference number 57 refers to a random noise floor determined by imaging device and is independent of the light intensity. The reference number 56 refers to photon-related noise comprising fixed pattern noise and random noise that increases as the intensity of the incident light increases. The superposition of the noise 56 and the noise 57 forms the overall noise in the imaging system. The reference number 51 refers to the photoelectric response of the first subpixel 110, the reference number 52 refers to the photoelectric response of the second subpixel 210, the slopes of the two photoelectric response represent the photoelectric conversion efficiency or sensitivity of the two subpixel, respectively. Benefit from a thicker depletion layer and higher transmittance in color filter, the first subpixel 110 exhibits a higher efficiency of photoelectric conversion. In summary, if driving conditions of the two subpixels are kept the same, the first subpixel 110 will reach to saturation point earlier than the second subpixel 210, as the two saturation points S1 and S2 indicated. According to a reasonable assumption that effective signal detection starts from the point where the signal to noise ratio equals to one, the minimum detectable light intensity of the first subpixel 110 is at point N1, while the minimum detectable light intensity of the second subpixel 110 is at point N2. By combining the two output digitally, a wider dynamic range from point N1 to point S2 is realized in the multispectral imaging sensors of the present disclosure.

Figure 6:
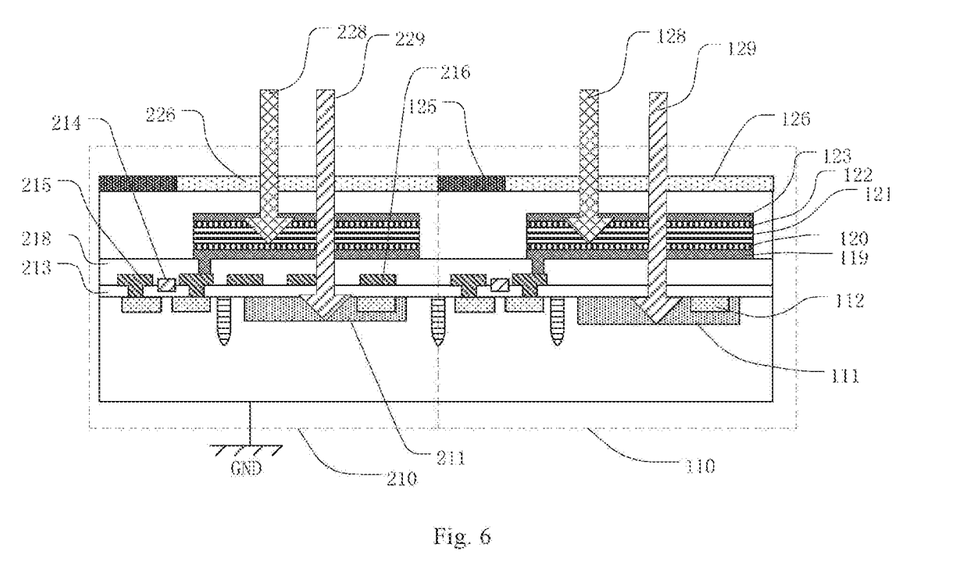
FIG. 6 is a cross-sectional view of a multispectral imaging device of a second embodiment of the present disclosure.

Shown in FIG. 6 is a cross-sectional view of the second embodiment of the present disclosure. One unique feature introduced in the second embodiment, is an addition of interlayer 216 between the first photodiode and the second photodiode in the second subpixel 210. The interlayer is made of an opaque material such as metal or any material which blocks or absorbs infrared light. In the case of metallic interlayer, the inter layer could be made together with the drain electrodes 215 of the switching transistor. The role of interlayer 216 is to reduce the intensity of the NIR light which could reach to the infrared light conversion layer 211, so as to decrease the infrared light sensitivity of the second subpixel 210 furthermore. In the embodiment, a metal interlayer with at least one through hole is provided to allow partial infrared light pass through. By enlarging the sensitivity discrepancy between the first subpixel and the second subpixel, as disclosed above, the multispectral imaging device is capable of dealing with wider dynamic range infrared images.

One possible variety of the embodiment shown in FIG. 6, is connecting the conductive interlayer 216 to an external fixed or controllable voltage, so to form additional storage capacitor for the visible light conversion layer and infrared light conversion layer in the second subpixel. The additional storage capacitor will increase the saturation level of the second subpixel and therefore further increase the dynamic range of the multispectral imaging device in the present disclosure.

Another possible variety evolved from the embodiment shown in FIG. 6, is to add interlayers for both the first subpixel and the second subpixel that the two interlayers have different infrared light transmittances. In more specifically, interlayers in the first and the second subpixels function as band-pass filter, or low-pass filter, or high-pass filter, and with different infrared pass-band or "colors", respectively. Since image signals from the first subpixel 110 and the second subpixel 210 are acquired independently, the multispectral imaging device in the present disclosure is therefore capable of distinguishing different "color" in the infrared images. Infrared light with different wavelengths reflected from human body, are actually representing the absorption or reflection characteristics in different subcutaneous depths and in different human tissues or blood vessels (veins, artery, or even the same kind of blood vessels but contain different hemoglobin densities), and carrying along extremely valuable image details of human skin and subcutaneous.

Another possible embodiment of the present disclosure, is to apply an antireflection film between the visible light conversion layer and the infrared conversion layer in the first subpixel 110, or alternatively to add functionality of antireflection in the interlayer in the first subpixel 110. By using the antireflection film, the first subpixel 110 will have larger infrared sensitivity comparing to the second subpixel 210, and hence result in a further enlarge the dynamic range of the multispectral imaging device in the present disclosure. The principles of the antireflection effects described above may be based on matching the indexes of reflection between two media at the reflection interface, or based on resonance of multireflection in microcavity. To satisfy the resonance conditions, the thickness of the antireflection film may be a quarter of the wavelength of NIR light, that is made in a range from 180 nm to 280 nm, corresponding to a NIR light waveband from 720 nm to 1120 nm. The antireflection film may consist of calcium fluoride coating.

The various embodiments and possible varieties describe above are realized in the approach of creating the difference of the infrared light conversion efficiency in the first subpixel and the second subpixel by the means of, changing the absorption depth of infrared light conversion layer, or using an interlayer film to attenuate infrared light, or using an infrared light antireflection film. Although each of these means can be applied alone, any combinations of two or three of the above means are within the scope of the present disclosure.

Figure 7:
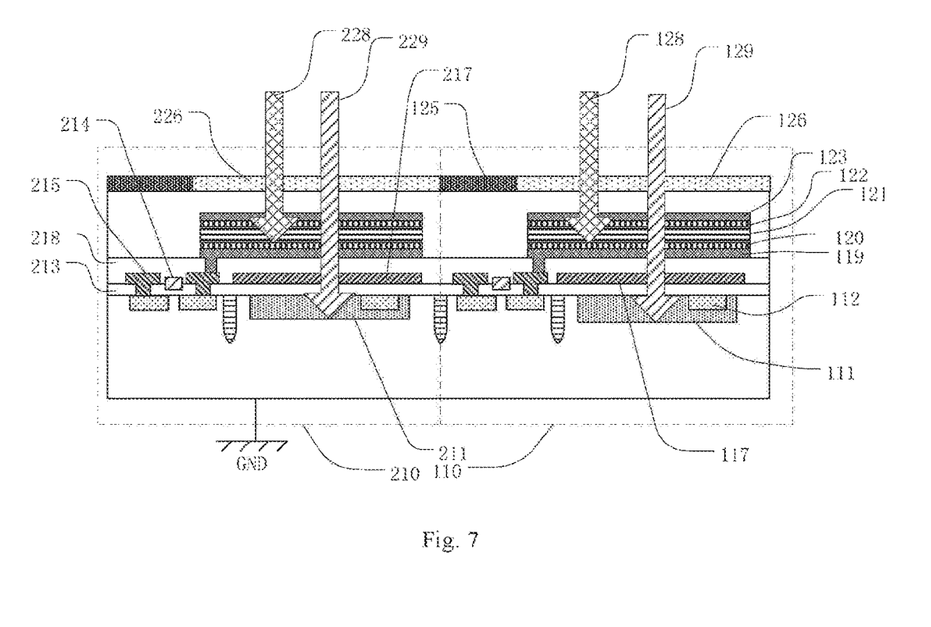
FIG. 7 is a cross-sectional view of a multispectral imaging device of a third embodiment of the present disclosure.

FIG. 7 shows a cross-sectional view of a multispectral imaging device of a third embodiment of the present disclosure.

In the third embodiment, interlayer made of transparent conductive films 117 and 217 are applied between the insulating layer 218 and the insulating layer 213 in both the first subpixel 110 and the second subpixel 210. One of the roles of these transparent interlayer 117 and 217 is to form a electrostatic shield between the visible light conversion layer and the infrared lightconversion layer, to shield any electronic noise or cross-talk interference between them. Another role is to form an additional charge capacitor which contributes additional dynamic range of the multispectral imaging device. The NIR light transmittance of the transparent interlayer films 117 and 217 is made larger than 60% to allow most of the infrared light to pass through. The transparent interlayer can be made of ITO, SnO2, or thin polycrystalline silicon or microcrystalline silicon film.

To add controllability to the multispectral imaging device, the conductive interlayer 117 and 217 can be connected to different external or internal voltages, respectively. These arrangements can be applied in the embodiment shown in FIG. 1 where the two infrared light conversion layers have different thicknesses. The light conversion layer is developed in silicon bulk where the electrons or holes are depleted. The depletion thickness can be modified by electric field, and therefore be controlled by the voltages on the transparent interlayer.

Combinations of the electrically controllable transparent interlayer described above, with infrared light filter or antireflection layer, may generate some additional structures with different dynamic ranges, supporting various applications. Consider pixel layout design, connecting the transparent interlayer 117 and/or 217 to the signal output lines of the subpixel may reduce the layout complexity and increase the effective aperture for incident light.

Figure 8:
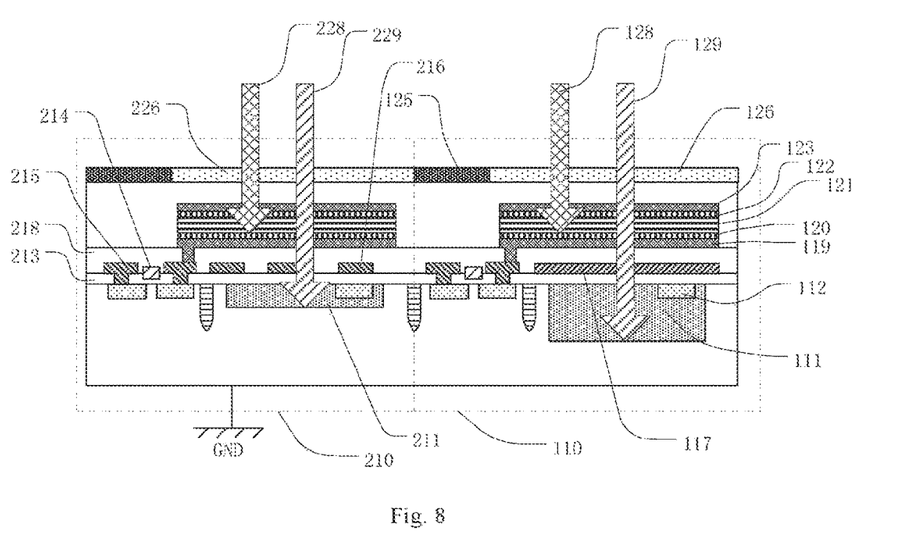
FIG. 8 is a cross-sectional view of a multispectral imaging device of a fourth embodiment of the present disclosure.

Shown in FIG. 8 is a cross-sectional view of a multispectral imaging device according to a fourth embodiment of the present disclosure, where several features disclosed above are combined. First of all, the thickness of the depletion layer 111 in the first subpixel is larger than the thickness of the depletion layer 211 in the second subpixel 210; secondly, a metallic interlayer film 216 which partially blocks or absorbs infrared light is inserted between insulators 218 and 213 in the second subpixel 210, while an transparent conductive interlayer film 117 is inserted between insulators 218 and 213 in the first subpixel 110; third, a green or blue filter 226 is on top of the second subpixel 210, and a red filter 126 is on top of the first subpixel 110. The interlayer film 216 and 117 can be connected to different voltages, respectively; or alternatively one interlayer film is connected to an external voltage source, while another is kept electrically floating.

Figure 9:
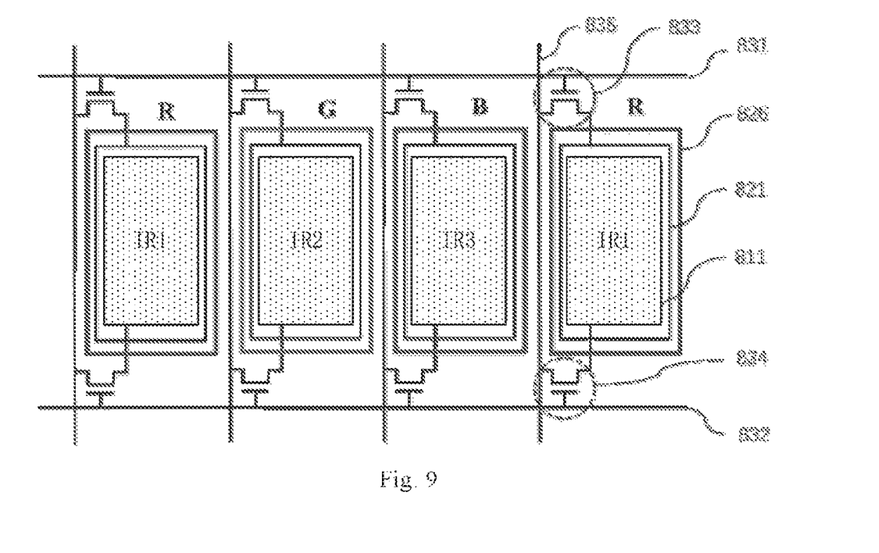
FIG. 9 is a cross-sectional view of a multispectral imaging device of a fifth embodiment of the present disclosure.

Shown in FIG. 9, is a schematic view of a multispectral imaging device of a fifth embodiment of the present disclosure.

Each subpixel comprises a first photodiode 811 to sense infrared light, a second photodiode 821 to sense visible light, a color filter 826, a first switching transistor 833 controlling signal output from photodiode 821, and a second switching transistor 834 controlling signal output from photodiode 811. A scan line 831 controls the gate electrode of the first switching transistors and performs the same for all other subpixels. The scan line 832 controls the gate electrode of the second switching transistor and performs the same for all other subpixels on the same row. By scanning the entire pixel array row by row, the visible light signal and infrared light signal charges are read out from the subpixels alternatively through data line column 835. Black matrix film has openings on each subpixel as indicated by the rectangular window 826 in the FIG. 9. The black matrix film allows the incident light pass through the openings, but blocks the light photons striking on the rest area that could reach to the infrared light conversion layer down below.

The switching transistors described previously can be replaced by an APS (active pixel sensor) type pixel circuit, typically comprising three transistors in each unit, a switching transistor, an amplifying transistor and a reset transistor. The amplifying transistor converts photo-generated charges either by visible light or by infrared light into signal voltage to be output, with its gate electrode connected to the photoelectric conversion layer. The switching transistor connects amplifying transistor and output data line, to output signal voltage to external processing circuit. The reset transistor connects the gate electrode of the amplifying transistor and external reset voltage, to periodically reset the potential of the gate electrode of the amplifying transistor after each signal readout cycle.

According to the transmittance plots shown in FIG. 2, each color filter has different transmittances in the NIR light waveband, therefore the subpixel array can be arranged in a manner that a color filter in higher infrared light transmittance is combined with a deeper depletion layer, and with an interlayer in less attenuation in infrared light waveband. This arrangement is also applicable to image array with multiple color schemes such as RGB or RGBW pattern.

It should be stated that, the embodiments described previously are representing one or several aspects in arrangements, combinations and features of the present disclosure, but not limit the scope of the present disclosure. The semiconductor devices shown in the figures include at least four technical aspects: circuits and structure; manufacture process and processing parameters; materials of semiconductors, metals and insulating films; actuating methods in actual use. The contents disclosed in the four aspects and with various combinations or varieties thereof, should all be understood to be in accordance with the basic conception of the present disclosure. Other semiconductor materials, include polycrystal silicon, microcrystal silicon, amorphous selenium, semiconductor of III-V system, semiconductor of II-IV system, metal oxide semiconductor, and etc. can be used to replace the a-SiH as the visible light conversion material. The transistors in each subpixel may also be replaced by low temperature polycrystal silicon TFT (LTPS TFT), metal oxide semiconductor such as IGZO TFT, CdTe TFT, organic semiconductor TFT, and etc.

On that account, by providing the arrangement method with color filters and a plurality of combinations with infrared pixel matrix having different detection sensitivity, the multispectral imaging device of the present disclosure may broaden the detecting dynamic range by increasing the detecting sensitivity and raise the detecting upper limits or saturation level. The multispectral imaging device may respectively collect and process infrared images in multiple spectral ranges, remove the background noise, and acquire infrared image at different depths under skins.

The basic concept and a plurality of embodiments of the present disclosure are described above. Here a statement need to be made that the present disclosure is not limited by the above specific embodiments, the person skilled in the art may make all kinds of transformations and amendments and combinations within the scope of claims, which will not influence the actual contents of the present disclosure. The present disclosure is also not limited to medical imaging application as described in the present disclosure, it may also be used in other fields such as industrial and agriculture products, environment monitoring and diagnosis, recognition of personal identity, instruments in gaming industry, virtual reality and augmented reality and etc.

What is claimed is:

1. A multispectral imaging device, comprising a pixel array, said pixel array comprises a plurality of pixels arranged repeatedly and periodically, each said pixel at least comprises a first subpixel and a second subpixel, said first subpixel and said second subpixel at least respectively comprises:
   an infrared light conversion layer, to convert NIR light photons into electrons;
   a visible light conversion layer, to convert visible light photons into electrons; and
   a color filter layer, to selectively transmit light in specific color, said visible light conversion layer arranged between said infrared light conversion layer and said color filter layer;
   wherein, conversion efficiency of the infrared light conversion layer in said first subpixel is larger than conversion efficiency of the infrared light conversion layer in said second subpixel, and infrared light transmittance of the color filter layer in said first subpixel is larger than infrared light transmittance of the color filter layer in said second subpixel.

2. The multispectral imaging device according to claim 1, wherein, following a direction of incident light, within each said subpixel, said color filter layer completely covers said visible light conversion layer, said visible light conversion layer completely covers said infrared light conversion layer.

3. The multispectral imaging device according to claim 1, wherein, said infrared light conversion layer comprises a first photodiode, said visible light conversion layer comprises a second photodiode, said first photodiode is a PN type photodiode, and said second photodiode is a PIN type photodiode.

4. The multispectral imaging device according to claim 1, wherein, said infrared light conversion layer comprises an electron or hole depletion layer in the bulk of a semiconductor substrate, wherein,
   said electron or hole depletion layer is composed of a depletion layer formed in one or two doped layers being completely or partially depleted.

5. The multispectral imaging device according to claim 4, wherein, the thickness of said electron or hole depletion layer in said first subpixel is larger than the thickness of said electron or hole depletion layer in said second subpixel.

6. The multispectral imaging device according to claim 5, wherein, the thickness of said electron or hole depletion layer in said first subpixel is in a range of 5 um to 100 um; the thickness of said electron or hole depletion layer in said second subpixel is in a range of 1 um to 10 um.

7. The multispectral imaging device according to claim 1, wherein, the color filter layer of said first subpixel comprises a filter transmitting red light, the color filter layer of said second subpixel comprises a filter transmitting green or blue light.

8. The multispectral imaging device according to claim 1, wherein, said multispectral imaging device further comprises:
   an opaque film, arranged between adjacent color filters to block light that striking on said opaque film, the width of said opaque film larger than or equal to the space gap between adjacent visible light conversion areas.

9. The multispectral imaging device according to claim 1, wherein, at least one subpixel comprises:
   a conductive or non-conductive interlayer film, arranged between said visible light conversion layer and said infrared light conversion layer, used to partially block or partially absorb NIR light.

10. The multispectral imaging device according to claim 9, wherein, said interlayer film is a conductive film connected to a fixed or a tunable voltage to form a capacitance coupling to said infrared light conversion layer and said visible light conversion layer.

11. The multispectral imaging device according to claim 9, wherein, said interlayer film comprises a plurality of pieces or one piece with at least one through hole.

12. The multispectral imaging device according to claim 9, wherein, said interlayer is placed in said second subpixel, but not placed in said first subpixel.

13. The multispectral imaging device according to claim 1, wherein, at least one subpixel comprises:
   an interlayer with antireflection functions in NIR light waveband, arranged between said visible light conversion layer and said infrared light conversion layer.

14. The multispectral imaging device according to claim 13, wherein, said interlayer with antireflection functions in NIR waveband is placed in the first subpixel, but not placed in the second subpixel.

15. The multispectral imaging device according to claim 13, wherein, the thickness of said interlayer with antireflection functions in NIR light waveband is ranging from 180 nm to 280 nm.

16. The multispectral imaging device according to claim 1, further comprising:
   a plurality of output signal lines arranged vertically and a plurality of scan lines arranged horizontally, said output signal lines and said scan lines crossing each other and define said subpixel;
   each said subpixel comprises a first switching transistor, controlled by one horizontal scan line and used to read out visible light signal; and a second switching transistor, controlled by another horizontal scan line and used to read out infrared light signal.

17. The multispectral imaging device according to claim 16, wherein every two or three or four said subpixels form a pixel unit, and said pixel unit is formed in a manner, that according to ranking sequence of infrared light transmittance from large to small for the color filters of the subpixels, and ranking sequence of the conversion efficiency from large to small for the infrared light conversion layer, combing the color filter having higher infrared light transmittance with the infrared light conversion layer having higher infrared light conversion efficiency.

18. The multispectral imaging device according to claim 1, wherein, a plurality of means can be adopted or combined to form subpixels having different infrared light conversion efficiency, and the said means at least comprise:
   modifying the absorption depth of the infrared light conversion layer;
   adding an interlayer with different infrared light transmission based on the principles of reflection or absorption or antireflection, between the visible light conversion layer and the infrared light conversion layer;
   adding an conductive interlayer between the visible light conversion layer and the infrared light conversion layer; and
   connecting said conductive interlayer to a voltage source to form capacitors with visible light conversion layer and with infrared light conversion layer.

19. The multispectral imaging device according to claim 18, wherein, in each said pixel, at least two of said subpixels have said conductive interlayers, and said conductive interlayers are connected to different voltages respectively.

20. The multispectral imaging device according to claim 18, wherein, said conductive interlayer comprises at least one of the following materials: ITO, SnO2, ZnO2 or other metallic oxides, polysilicon or microcrystal silicon, and is capable of transmitting NIR light.

21. The multispectral imaging device according to any claims from claim 1, wherein, each said subpixel further comprises a photoelectric conversion layer, an APS circuit or a circuit comprising amplifying transistor converting photo-generated charges to signal voltage; a switching transistor to output signal voltage; and a reset transistor to reset the gate voltage of said amplifying transistor.

* * * * *